(12) United States Patent
Chandramowli et al.

(10) Patent No.: US 8,580,920 B2
(45) Date of Patent: Nov. 12, 2013

(54) PEPTIDES USEFUL FOR SKIN LIGHTENING

(75) Inventors: Ganesh Chandramowli, Bangalore (IN); Babu Rakesh Kumar Bandi, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/515,074

(22) PCT Filed: Nov. 23, 2010

(86) PCT No.: PCT/EP2010/067972
§ 371 (c)(1),
(2), (4) Date: Jun. 11, 2012

(87) PCT Pub. No.: WO2011/072991
PCT Pub. Date: Jun. 23, 2011

(65) Prior Publication Data
US 2012/0263665 A1  Oct. 18, 2012

(30) Foreign Application Priority Data

Dec. 16, 2009 (IN) .................... 2898/MUM/2009

(51) Int. Cl.
| | |
|---|---|
| A61K 38/12 | (2006.01) |
| A61K 38/04 | (2006.01) |
| A61K 38/00 | (2006.01) |
| A61K 38/08 | (2006.01) |
| A61K 8/00 | (2006.01) |
| A61K 8/18 | (2006.01) |
| C07K 5/00 | (2006.01) |
| C07K 7/00 | (2006.01) |
| C07K 16/00 | (2006.01) |
| C07K 17/00 | (2006.01) |
| A61P 17/00 | (2006.01) |
| A61Q 5/08 | (2006.01) |
| A61Q 19/02 | (2006.01) |

(52) U.S. Cl.
USPC .......... 530/317; 530/321; 530/327; 514/18.6; 514/18.8; 514/21.1; 514/21.6; 424/62

(58) Field of Classification Search
None
See application file for complete search history.

(56) References Cited

U.S. PATENT DOCUMENTS

| | | | |
|---|---|---|---|
| 5,126,327 A | 6/1992 | Takeuchi | |
| 7,344,860 B2 | 3/2008 | Franco | |
| 2007/0060743 A1* | 3/2007 | Tang et al. | .................... 536/23.1 |
| 2011/0045036 A1* | 2/2011 | Lintner et al. | ................ 424/401 |

FOREIGN PATENT DOCUMENTS

| | | |
|---|---|---|
| EP | 389950 | 10/1990 |
| WO | WO 9912518 A1 * | 3/1999 |
| WO | WO 2008148545 A1 * | 12/2008 |

OTHER PUBLICATIONS

UniProt Database, Accession No. A8Y9L6 (Jan. 2008).*
Wang et al., "Synthesis of small cyclic peptides containing the disulfide bond," ARKIVOC, pp. 1-7 (2006).*
Jan. 15, 2008, UniProt, UniProt Consortium Jan. 2008, ., ., Creative Commons Attribution.
Le Pape Elodie, Aug. 2008, Regulation of eumelanin / pheomelanin synthesis and visible pigmentation in melanocytes by ligands of the melanocortin 1 receptor, Regulation of eumelanin/pheomelanin synthesis, 21, No. 4, 477-486.
PCT International Search Report in PCT application PCT/EP2010/067972 dated Feb. 25, 2011 with Written Opinion.
Abstract of WO 01/88088 published Nov. 21, 2001.
Abstract of WO02008034648 published Mar. 27, 2008.

* cited by examiner

Primary Examiner — Marcela M Cordero Garcia
Assistant Examiner — Thea D'Ambrosio
(74) Attorney, Agent, or Firm — Michael P. Aronson

(57) ABSTRACT

The present invention relates to novel peptides and to topical and food compositions comprising them. The novel peptides have applications in skin lightening and immunomodulation when applied topically and to immunomodulation and modulation of body mass when consumed in food compositions.

7 Claims, No Drawings

PEPTIDES USEFUL FOR SKIN LIGHTENING

This is application is a national stage application under 35 U.S.C. §371 of PCT International Application PCT/EP2010/067972 filed Nov. 23, 2010, which claims priority under 35 U.S.C. §119 to Indian Application 2898/MUM/2009 filed Dec. 16, 2009; all of which are incorporated herein in their entirety, by reference.

TECHNICAL FIELD

The present invention relates to novel peptides and to topical and food compositions comprising them. The novel peptides have applications in skin lightening and immunomodulation when applied topically and to immunomodulation and modulation of body mass when consumed in food compositions.

BACKGROUND OF THE INVENTION

People all over the world want to be healthy and look healthy. Having a good and balanced lifestyle comprising eating wholesome food, exercise, and minimizing external stresses like pollution, heat, dust, and ultra-violet (uv) radiation have been believed to give one a healthy body. In addition to the above lifestyle changes which also make a person look healthy, people use cosmetics to improve their external appearance. Two of the most important attributes to being healthy and looking healthy is a controlled body weight (not too overweight or too underweight) and external appearance of the exposed skin. While nutrition plays an important part in having a controlled body weight, external appearance is to an extent controlled by use of topically applied cosmetic products.

In tropical countries where people generally have dark skin, there is a desire to have lighter skin appearance. People who live far from the tropical areas e.g. the Caucasian people who generally have lighter skin, prefer to have an even tanned tone of their skin. Any exposure of their skin to sunlight, often leads to blotchy skin, referred to as freckles and in some cases they experience hyperpigmentation in localized areas of the skin.

To have lighter coloured or even toned skin colour, many cosmetic approaches are taken. One common approach is to include sunscreens or sunblocks in the cosmetic compositions. Sunscreens are generally organic compounds that work by absorbing ultra-violet radiation from the sun at a specified wavelength range thus not permitting the uv radiation from reaching the skin surface. UV radiation is believed to be the cause of skin coloration or tanning and if such tanning is uneven, it is disliked by the consumer. Sunblocks are generally inorganic compounds that act as physical barrier against a wide range of radiation from the sun (both uv and visible light).

Another approach is to include a skin lightening active in the cosmetic composition. Skin lightening actives are usually molecules or compositions which alter the formation of melanin in the skin through biochemical transformation in the skin thereby changing the colour and appearance of the skin. In human skin, formation of melanin pigment is initiated by the polymerization of the amino acid L-tyrosine, through a set of enzyme catalyzed as well as spontaneous chemical reactions. Amongst other things, this involves the action of the enzyme tyrosinase, present within the melanosomal compartment of melanocytes. Melanosomal contents are transferred from the melanocyte to multiple surrounding keratinocytes. The overall process is influenced by many hormones of which the melanocyte stimulating hormone (MSH), is a well studied one.

The present inventors have been working on developing novel skin lightening actives or new compositions for providing a skin lightening benefit. In the present invention, they have taken the approach to provide for novel peptides which preferentially bind to α-MSH (α-melanocyte stimulating hormone) so as to inhibit the binding of α-MSH on to the melanocortin 1 receptor (MC1 R). This inhibition provides benefits in the area of skin lightening. Use of peptides different from those disclosed herein for skin lightening which involve targeting the melanocyte have been disclosed earlier.

JP 2001 002527 (Lion) discloses a skin preparation for external use which includes 0.000001-30 weight percent based on total composition of a cell adhesion rearranging agent for melanocyte, e.g. peptides including Arginine-Glycine-Aspartic acid (RGD) sequence, peptides including an amino acid sequence of tyrosine-isoleucine-glycine-serine-arginine, pentoxyfeline, 3-deazaadenosine, derivatives of carboxamido, inositol polyamines, derivatives of salicylic acid and triterpenic acid, lactose, etc.

U.S. Pat. No. 5,126,327 (Lion) discloses a melanocyte-stimulating hormone inhibitor which has an amino acid sequence represented by formula [I], [II] or [III] as defined in the reference. It claims a melanocyte-stimulating hormone inhibitor and an external preparation to be applied to the skin which contains the inhibitor which prevent or cure the symptoms of chloasmata and freckles caused by an excess production of melanin by enhanced melanocyte function.

The present inventors have identified novel peptides which may be easily synthesized and may additionally provide synergistic benefits when used together. They found through extensive research involving a phage display technique that two specific peptides of seven amino acid sequence, specifically: Peptide (i) which has a specific low molecular weight (700 to 20 000) which has an amino acid residue of SEQ ID NO:1 -Leu-Ser-Arg-His-Val-Leu-Gln- (LSRHVLQ); or peptide (ii) having the amino acid residue of SEQ ID NO:2 -His-Gly-His-Pro-Phe-Ala-Pro- (HGHPFAP) preferentially bind to a-MSH (a- melanocyte stimulating hormone) so as to inhibit the binding of aMSH 0 n to M C 1 R. Further these peptides also have benefits in immunomodulation and modulation of body mass when they are used in topical or food compositions.

A search using basic local alignment search tool (BLAST) protein database search programs in the National Centre for Biotechnology Information (NCBI) database indicates that the exact same sequence of seven amino acids in peptide (i) has been reported as a part of a large protein or polynucleotide in natural occurring materials e.g in U.S. Pat. No. 7,344,860 (Bristol Myers Squibb Co.) and WO 2008 034648 (Metanomics). However the sequences reported therein have a molecular weight in excess of 27 000 Daltons and sometimes as high as 65 000 Daltons and do not provide the skin lightening and other benefits envisaged in the present invention. The inventors are not aware of the peptide (ii) being disclosed before.

It is thus an object of the present invention to provide for novel peptides which provide for skin lightening when incorporated in skin lightening products.

It is another object of the invention to provide for novel peptides which interact synergistically to provide for enhanced skin lightening as compared to the individual peptides when incorporated in skin lightening products.

It is yet another object of the present invention to provide for novel peptides which may be incorporated in topical or food products that provides for benefits like immunomodulation and/or modulation of body mass.

SUMMARY OF THE INVENTION

According to the first aspect of the present invention there is provided a peptide selected from
(i) Peptide (i) having SEQ ID NO:1 having molecular weight from 700 to 20 000 Daltons which comprises the amino acid residue -Leu-Ser-Arg-His-Val-Leu-Gln-(LSRHVLQ); or
(ii) Peptide (ii) having SEQ ID NO:2 comprising the amino acid residue -His-Gly-His-Pro-Phe-Ala-Pro-(HGHPFAP).

According to a preferred aspect of the present invention there is provided a skin lightening composition comprising a peptide of the first aspect of the present invention along with a cosmetically acceptable base.

According to another aspect of the invention there is provided use of a peptide of the first aspect of the invention for lightening of skin.

According to another aspect of the invention there is provided use of a peptide of the first aspect of the invention for immunomodulation.

According to another aspect of the invention there is provided use of a peptide of the first aspect of the invention for modulation of body mass.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. The disclosure of the invention as found herein is to be considered to cover all embodiments as found in the claims as being multiply dependent upon each other irrespective of the fact that claims may be found without multiple dependency or redundancy.

DETAILED DESCRIPTION OF THE INVENTION

In the present invention is claimed two peptides i.e. peptide (i) having SEQ ID NO:1 or peptide (ii) having SEQ ID NO:2. These two novel peptides preferentially bind to α-MSH (α-melanocyte stimulating hormone) so as to inhibit the binding of α-MSH onto the MC1R. This inhibition provides benefits in the area of skin lightening, immunomodulation and modulation of body mass when these peptides are used in topical or food compositions. These two peptides were identified using the phage display (PD) technique, a methodology in the biotechnology domain used to identify peptides which specifically bind a target molecule. The entire process to shortlist the two peptides from about a billion possibilities comprised the steps show below:

Immobilization of α-MSH to plastic plates

↓

Phage display bio-panning steps (New England Biolabs) on immobilized α-MSH

↓

Sequencing of binding/eluted phages
(Elimination of plastic binders and choose only those which preferentially bind α-MSH)

From the very large number of possible peptides (of about a billion possibilities), seven unique peptides were first identified as potential α-MSH binders. Of these seven peptides, two peptides were found to have exceptionally strong binding to the α-MSH binders and these two were selected for studying the functional benefit. The functional efficacy i.e. potential to decrease melanin content of these peptides was then tested in a melanin content assay. Not only were these two peptides confirmed to provide a reduction in melanin content but they were also seen to interact synergistically when used together.

Peptide (i) having SEQ ID NO:1 comprises seven amino acids in a specific sequence i.e. -Leu-Ser-Arg-His-Val-Leu-Gln-. It is important that Peptide (i) having SEQ ID NO:1 has a molecular weight between 700 and 20 000 Daltons. The molecular weight of the peptide (i) having SEQ ID NO:1 is preferably lower than 18 000 Daltons, more preferably lower than 15 000 Daltons, furthermore preferably lower than 12 000 Daltons. The molecular weight of the peptide (i) having SEQ ID NO:1 is preferably higher than 750 Daltons, more preferably higher than 1000 Daltons, further more preferably higher than 2000 Daltons, and most preferably higher than 4500 Daltons. It is envisaged that preferred ranges encompass any combination of the lower preferred limit on molecular weight with any one of the preferred upper preferred limit of the molecular weights listed above. It is especially preferred that the peptide (i) having SEQ ID NO:1 has a molecular weight between 1000 and 8000 Daltons. The advantage of having the molecular weight of peptide (i) having SEQ ID NO:1 in the above ranges is that with peptides of such short chain length, it is more probable that this peptide binds to the α-MSH (α-melanocyte stimulating hormone) thereby inhibiting the binding of α-MSH onto the MC1R. The probability of proteins having the amino acid sequence claimed in the present invention binding to α-MSH is very low if not improbable when the molecular weight of the protein is higher than 20 000 and is therefore not claimed.

It is preferred that peptide (i) having SEQ ID NO:1 comprises the cyclic amino acid residue -Cys-Leu-Ser-Arg-His-Val-Leu-Gln-Cys-
|_____S_____S_____| i.e. the 7 member amino acid residue has a cystine at either end which are bonded together through a di-sulphide bond. This preferred aspect of the peptide is referred to herein as peptide (iii) having SEQ ID NO:3.

It is further preferred that the peptide (i) having SEQ ID NO:1 comprises the amino acid residue

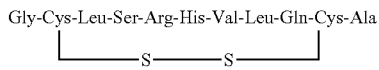

The above peptide is referred to herein as peptide (iv) having SEQ ID NO:4. This peptide is especially preferred since this is observed to be more stable.

The peptide (ii) having SEQ ID NO:2 which comprises the amino acid sequence -His-Gly-His-Pro-Phe-Ala-Pro is also claimed in the present invention. Although there is no limit on the molecular weight of this peptide for the various uses claimed in the present invention, it is preferred that the peptide (ii) has a molecular weight between 700 and 20 000 Daltons. The molecular weight of the peptide (ii) having SEQ ID NO:2 is preferably lower than 18 000 Daltons, more preferably lower than 15 000 Daltons, further more preferably lower than 12 000 Daltons. The molecular weight of the peptide (ii) having SEQ ID NO:2 is preferably higher than 750 Daltons, more preferably higher than 1000 Daltons, further more preferably higher than 2000 Daltons, and most preferably higher than 4500 Daltons.

It is preferred that the peptide (ii) having SEQ ID NO:2 comprises the cyclic amino acid residue

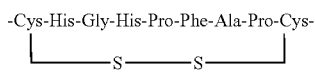

i.e. the 7 member amino acid residue has a cystine at either end which are bonded together through a di-sulphide bond. The above peptide is referred to herein as peptide (v) having SEQ ID NO:5.

It is further preferred that peptide (ii) having SEQ ID NO:2 comprises the amino acid residue

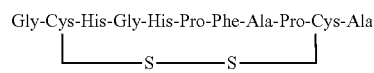

The above peptide is referred to herein as peptide (vi) having SEQ ID NO:6. As with peptide (iv) having SEQ ID NO:4, it is found that presence of a -Gly- amino acid at one end and a -Ala- amino acid at the other end, provides for better stability of the peptide (vi) when used in composition for consumer use.

The aforementioned amino acid sequences are summarized in table 1 wherein each X is selected from the group consisting of twenty amino acids (of which other than glycine, the rest are L-isomers in proteins):

| | | |
|---|---|---|
| Glycine | Gly | G |
| Alanine | Ala | A |
| Valine | Val | V |
| Leucine | Leu | L |
| Isoleucine | Ile | I |
| Serine | Ser | S |
| Threonine | Thr | T |
| Phenylalanine | Phe | F |
| Tyrosine | Tyr | Y |
| Tryptophan | Trp | W |
| Cysteine | Cys | C |
| Proline | Pro | P |
| Histidine | His | H |
| Glutamic acid | Glu | E |
| Aspartic Acid | Asp | D |
| Glutamine | Gln | Q |
| Asparagine | Asn | N |
| Lysine | Lys | K |
| Arginine | Arg | R |
| Methionine | Met | M | and m and n are each independently an integer from 0 to 10, preferably from 0 to 5, more preferably from 0 to 2.

TABLE 1

| | Amino acid sequences | |
|---|---|---|
| Seq ID | short | long |
| 1. | $X_m$-LSRHVLQ-$X_n$ | -Leu-Ser-Arg-His-Val-Leu-Gln- |
| 2. | $X_m$-HGHPFAP-$X_n$ | -His-Gly-His-Pro-Phe-Ala-Pro- |
| 3. | $X_m$-CLSRHVLQC-$X_n$ S-S bond between C-C | -Cys-Leu-Ser-Arg-His-Val-Leu-Gln-Cys- S-S bond between C-C |
| 4. | $X_m$-GCLSRHVLQCA-$X_n$ S-S bond between C-C | -Gly-Cys-Leu-Ser-Arg-His-Val-Leu-Gln-Cys-Ala- S-S bond between C-C |
| 5. | $X_m$-CHGHPFAPC-$X_n$ S-S bond between C-C | -Cys-His-Gly-His-Pro-Phe-Ala-Pro-Cys- S-S bond between C-C |
| 6. | $X_m$-GCHGHPFAPCA-$X_n$ S-S bond between C-C | -Gly-Cys-His-Gly-His-Pro-Phe-Ala-Pro-Cys-Ala- S-S bond between C-C |

It is further preferred that either of peptide(i) having SEQ ID NO:1 or peptide (ii) having SEQ ID NO:2 is derivatised with a skin substantive polymer. Suitable skin substantive polymers include polyethylene glycols.

According to another aspect of the present invention there is provided a skin lightening composition comprising a peptide as claimed in the first aspect of the present invention and a cosmetically acceptable base.

Skin lightening composition as used herein, is meant to include a composition for topical application to skin humans for getting skin lightening benefits. Such a composition may be generally classified as leave-on or rinse off. The composition of the present invention can be in the form of a liquid, lotion, cream, foam, scrub, gel, soap bar or toner, or applied with an implement or via a face mask, pad or patch. Non-limiting examples of skin lightening compositions include leave-on skin lotions and creams, shower gels, toilet bars, antiperspirants, deodorants, lipsticks, foundations, mascara, sunless tanners and sunscreen lotions. "Skin" as used herein is meant to include skin on the face and body (e.g. neck, chest, back, arms, underarms, hands, legs, buttocks and scalp).

The skin lightening composition preferably comprises from 0.0001 to 10 weight peptide of the invention. The more preferred amount of the peptide is from 0.001 to 3 weight %, further more preferred amount being from 0.001 to 1 weight %.

The skin lightening composition of the invention comprises a cosmetically acceptable base. The cosmetically acceptable base is preferably in the form of a cream, lotion, gel or emulsion.

The skin lightening composition of the invention may be prepared using different cosmetically acceptable emulsifying or non-emulsifying systems and vehicles. A highly suitable cosmetically acceptable base is in the form of a cream. Vanishing creams are especially preferred. Vanishing creams generally comprise 5 to 25% w/w fatty acid and 0.1 to 10% w/w soap. Vanishing creams give a highly appreciated matty feel to the skin. C12 to C20 fatty acids are especially preferred, further more preferred being C14 to C18 fatty acids. The most preferred fatty acid is stearic acid. The fatty acid in the composition is more preferably present in an amount in the range of 5 to 20% by weight of the composition. Soaps include alkali metal salts of fatty acids, like sodium or potassium salts, most preferred being potassium stearate. The soap is generally present in an amount in the range of 0.1 to 10%, more preferably 0.1 to 3% by weight of the composition. Generally a vanishing cream is prepared by taking a desired amount of total fatty matter and mixing with potassium hydroxide in desired amounts. The soap is usually formed in-situ during the mixing.

The skin lightening composition may comprise skin lightening agents other than the peptides claimed in the present invention. Other suitable skin lightening agent include vitamin B3 or its derivative e.g. niacin, nicotinic acid or niacinamide or other well known skin lightening agents e.g. aloe extract, ammonium lactate, arbutin, azelaic acid, kojic acid, butyl hydroxy anisole, butyl hydroxy toluene, citrate esters, 3 diphenyl propane derivatives, 2,5-dihydroxybenzoic acid and its derivatives, ellagic acid, fennel extract, gluco pyranosyl-1-ascorbate, gluconic acid, glycolic acid, green tea extract, hydroquinone, 4 hydroxyanisole and its derivatives, 4-hydroxy benzoic acid derivatives, hydroxycaprylic acid, lemon extract, linoleic acid, magnesium ascorbyl phosphate, mulberry root extract, 2,4 resorcinol derivatives, 3,5 resorcinol derivatives, salicylic acid, vitamins like vitamin B6, vitamin B12, vitamin C or vitamin A, a dicarboxylic acid, resorcinol derivatives, hydroxycarboxylic acid like lactic acid and their salts e.g. sodium lactate, and mixtures thereof. Vitamin B3 compound or its derivative e.g. niacin, nicotinic acid or niacinamide are the more preferred other skin lightening agents, most preferred being niacinamide. Niacinamide, when used, is preferably present in an amount in the range of 0.1 to 10%, more preferably 0.2 to 5% by weight of the composition.

The skin lightening composition may preferably additionally comprise one or more uv sunscreens. The uv sunscreens may be inorganic or organic.

A wide variety of organic sunscreen agents are suitable for use in combination with the essential ingredients of this invention. Suitable UV-A/UV-B sunscreen agents include, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethylaminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, butylmethoxydibenzoylmethane, 2-hydroxy-4-methoxybenzophenone, octyldimethyl-p-aminobenzoic acid and mixtures thereof. Most suitable organic sunscreen are 2-ethylhexyl-p-methoxycinnamate and butylmethoxydibenzoylmethane.

A safe and effective amount of sunscreen may be used in the skin lightening composition of the present invention. The composition preferably comprises from about 0.1% to about 10%, more preferably from about 0.1% to about 5%, of a sunscreen agent.

Useful inorganic sunblocks are also preferably used in the present invention. These include, for example, zinc oxide iron oxide, silica, such as fumed silica, and titanium dioxide.

Ultrafine titanium dioxide in either of its two forms, namely water-dispersible titanium dioxide and oil-dispersible titanium dioxide is especially suitable for the invention. Water-dispersible titanium dioxide is ultra-fine titanium dioxide, the particles of which are non-coated or which are coated with a material to impart a hydrophilic surface property to the particles. Examples of such materials include aluminium oxide and aluminium silicate.

Oil-dispersible titanium dioxide is ultrafine titanium dioxide, the particles of which exhibit a hydrophobic surface property, and which, for this purpose, can be coated with metal soaps such as aluminium stearate, aluminium laurate or zinc stearate, or with organosilicone compounds.

By "ultrafine titanium dioxide" is meant particles of titanium dioxide having an average particle size of less than 100 nm, preferably 70 nm or less, more preferably from 10 to 40 nm and most preferably from 15 to 25 nm.

By topical application to the skin of a mixture of both water-dispersible ultrafine titanium dioxide and oil-dispersible ultrafine titanium dioxide, synergistically enhanced protection of the skin against the harmful effects of both UV-A and UV-B rays is achievable.

Ultrafine titanium dioxide is the preferred inorganic sunblock agent as per this invention. The total amount of sunblock that is preferably incorporated in the composition according to the invention is from 0.1 to 5% by weight of the composition.

The composition according to the invention may also comprise other diluents. The diluents act as a dispersant or carrier for other materials present in the composition so as to facilitate their distribution when the composition is applied to the skin.

Diluents other than water can include liquid or solid emollients, solvents, humectants, thickeners and powders. Examples of each of these types of vehicle, which can be used singly or as mixtures of one or more vehicles, are as follows:

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate and myristyl myristate;

Solvents, such as ethyl alcohol, isopropanol, acetone, ethylene glycol monoethyl ether, diethylene glycol monobutyl ether and diethylene glycol monoethyl ether;

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

The cosmetically acceptable base is usually from 10 to 99.9%, preferably from 50 to 99% by weight of the composition and can, in the absence of other cosmetic adjuncts, form the balance of the composition.

The composition of the invention may comprise a conventional deodourant base as the cosmetically acceptable base. By a deodourant is meant a product in the stick, roll-on, or propellant medium which is used for personal deodourant benefit e.g. application in the under-arm area which may or may not contain anti-perspirant actives.

Deodourant compositions can generally be in the form of firm solids, soft solids, gels, creams, and liquids and are dispensed using applicators appropriate to the physical characteristics of the composition.

Deodourant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% by weight of the composition and in many instances from 40 to 80%.

Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C.

Hydrophilic carrier liquids that can be employed in compositions herein commonly comprise water and/or a mono- or polyhydric alcohol or water-miscible homologue. Monohydric alcohols often are short chain, by which is meant that they contain up to six carbons, and in practice are most often ethanol or sometimes isopropanol. Polyhydric alcohols commonly comprise ethylene or propylene glycol, or a homologue can be employed such as diethylene glycol.

The compositions that remain in liquid form can be applied employing conventional applicators such as a roll-on or by being pumped or squeezed through a spray-generating orifice. Such compositions may be thickened, for example, using one or more thickeners described subsequently herein.

Compositions that are firm solids, commonly obtained by use of a gellant or structurant, can be applied employing a stick applicator and soft solids, gels and creams can be applied employing an applicator having a dispensing head provided with at least one aperture through which the soft solid, gel or cream can be extruded under mild pressure.

Suitable thickeners or gellants that may be used for achieving this is by use of water-soluble or dispersible materials of higher viscosity, including various of the emulsifiers, and/or thickened or gelled with water-soluble or water-dispersible polymers including polyacrylates, and water-soluble or dispersible natural polymers, such as water-soluble polysaccharide or starch derivatives, such as alginates, carageenan, agarose and water-dispersible polymers include cellulose derivatives.

The concentration of such polymers in the composition is often selected in the range of from 1 to 20%, depending on the extent of thickening or structuring required, and the effectiveness of the chosen polymer in the liquid/mixture.

One class of structurant which is desirable by virtue of its long standing proven capability to produce firm solids and more recently in making soft solids, comprises waxes. Herein, the term wax is employed to encompass not only materials of natural origin that are solid with a waxy feel and water-insoluble at 30-40° C., but melt at a somewhat higher temperature, typically between 50 and 95° C., such as beeswax, candelilla or carnauba wax, but also materials having similar properties. Such other waxes include hydrocarbon waxes, eg paraffin wax, mineral wax and microcrystalline wax; synthetic waxes, such as polyethylene of 2 000 to 10 000 Daltons; waxy derivatives or waxy components of natural waxes Mixtures of materials within each class of gellant/structurant can be employed.

When the deodorant composition employed herein comprises an aerosol composition, it contains a propellant in addition to a base composition as described herein above, commonly in a weight ratio of from 95:5 to 40:60, and in many formulations, the weight ratio is from 90:10 to 50:50.

The propellant is conveniently a low boiling point material, typically boiling below $-5°$ C., for example an alkane such as propane, butane or isobutane, and possibly containing a fraction of pentane or isopentane, or a hydrofluorocarbon or fluorocarbon of similar carbon content. During filling of the aerosol canister, the propellant gas is liquified by virtue of the elevated pressure that is generated therein.

The composition of the invention may additionally comprise an anti-perspirant active. Antiperspirant actives include metal salts of aluminum, zinc, zirconium and zirconium aluminum mixtures of sulfates, chlorides, chlorohydroxides, tetrachlorohydrex glycinates, alums, formates, lactates, benzyl sulfonates, succinates, phenol sulfonates and the like. Typical levels of antiperspirant/deodorant actives are from about 0% to about 35%, preferably from about 0% to about 25% by weight of the composition. The composition may further include a complexing agent such as an organic acid or derivative thereof that are capable of forming complexes with the antiperspirant metallic salt. Examples of such complexing agents include, but are not limited to acetic acid, propionic acid, oxalic acid, malonic acid, succinic acid, tartaric acid, glycine and the like together with their cosmetically acceptable salts. Typical levels of complexing agent are from about 0% to about 15%, preferably from about 0% to about 10% by weight of the composition.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

According to another aspect of the present invention there is provided a method of lightening skin comprising applying to the skin a peptide as claimed in the first aspect of the invention.

According to yet another aspect of the present invention there is provided use of a peptide of the first aspect of the invention for lightening of skin. This use is preferably non-therapeutic.

According to yet another aspect of the present invention there is provided use of a peptide of the first aspect of the invention for immunomodulation. This use may be therapeutic or non-therapeutic, preferably non-therapeutic.

According to yet another aspect of the present invention there is provided use of a peptide as claimed in claim 1 for modulation of body mass. This use may be therapeutic or non-therapeutic, preferably non-therapeutic.

The invention is now further described by way of the following non-limiting examples.

EXAMPLES

Examples 1 to 7

The ability of various materials to act as skin lightening agents was measured using the melanin content assay. The experiments were carried out as per the following procedure:

A 2:1 ratio mix containing 100 000 human epidermal keratinocytes neonatal (HeKn) (neonatal foreskin keratinocytes from Cascade Biologicals) and 50 000 human epidermal melanocytes neonatal darkly pigmented (HeMnDP) (darkly pigmenting cells neonatal foreskin melanocytes from Cascade Biologicals) were seeded per well, in a 24 well cell culture plate, to establish a co-culture system. After overnight incubation, cells were treated with fresh media containing the test actives (untreated or vehicle controls set up in parallel) and incubated for 72 hours after treatment. Then media was removed and replaced with 80 µl of dimethyl sulphoxide (DMSO). The plate was further incubated with DMSO for 1 hour at 65° C., after which the well contents were triturated and the same sample used to assay both for melanin content (read at 450 nm in a plate reader) and protein estimation (regular BiCinchoninic Acid method, kit from Peirce). % reduction in melanin was with respect to untreated control. The reduction in melanin content for the various materials is shown in table 2 below.

TABLE 2

| 0 | PEPTIDE ADDED | % REDUCTION IN MELANIN CONTENT |
|---|---|---|
| 1 | Untreated control | 0 |
| 2 | 42 µM Peptide 1 | 5 (±2) |
| 3 | 420 µM Peptide 1 | 22 (±3) |
| 4 | 46 µM Peptide 2 | 12 (±10) |
| 5 | 460 µM Peptide 2 | Cytotoxic |
| 6 | Mix of 42 µM Peptide 1 and 46 µM Peptide 2 | 43 (±2) |
| 7 | 100 µM Kojic acid | 19 (±1) |

In the above table peptide 1 refers to SEQ ID NO:4

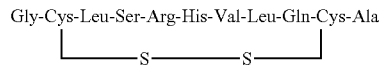

In the above table peptide 2 refers to SEQ ID NO:6

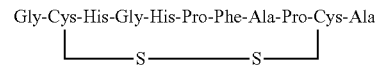

The data in table 2 indicates that the peptides as per the invention reduced melanin content thereby providing for skin lightening, which is comparable to agent used in the past e.g. kojic aicd. The data also illustrates synergistic interaction between the two peptides of the invention thereby giving enhanced skin lightening.

An independent set of experiments was carried out using methods similar to that described earlier, to study the reproducibility of the data. The data from this independent set of experiments confirmed the reproducibility.

---

The invention claimed is:

1. A stabilized cyclic peptide capable of providing skin lightening, said stabilized cyclic peptides selected from the group consisting of (i) a peptide sequence SEQ ID NO: 4

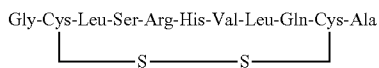

(ii) a peptide sequence SEQ ID NO: 6

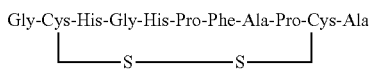

(iii) mixtures of peptide SEQ ID NO: 4 and peptide SEQ ID NO: 6.

2. The stabilized cyclic peptide according to claim 1, wherein the stabilized cyclic peptides is the mixture of peptide SEQ ID NO: 4 and peptide SEQ ID NO: 6.

3. The stabilized cyclic peptide according to claim 1, wherein the stabilized cyclic peptides is SEQ ID NO: 6.

4. The stabilized cyclic peptide as claimed in claim 1, wherein said peptide is derivatised with polyethylene glycol.

5. A skin lightening composition comprising the stabilized cyclic peptide as claimed in claim 1 and a cosmetically acceptable base.

6. The skin lightening composition as claimed in claim 5, comprising from 0.0001 to 10% by weight of said stabilized cyclic peptide.

7. A method of lightening skin comprising applying to the skin a peptide as claimed in claim 1.

* * * * *

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial
<220> FEATURE:
<223> OTHER INFORMATION: Peptide chemically synthesized.
<220> FEATURE:
<221> NAME/KEY: REPEAT
<222> LOCATION: (1)..(1)
<223> OTHER INFORMATION: 0 to 10 repeats, wherein Xaa represents any
      amino acid
<220> FEATURE:
<221> NAME/KEY: REPEAT
<222> LOCATION: (9)..(9)
<223> OTHER INFORMATION: 0 to 10 repeats, wherein Xaa represents any
      amino acid

<400> SEQUENCE: 1

Xaa Leu Ser Arg His Val Leu Gln Xaa
1               5
```

```
-continued

<210> SEQ ID NO 2
<211> LENGTH: 9
<212> TYPE: PRT
<213> ORGANISM: Artificial
<220> FEATURE:
<223> OTHER INFORMATION: Peptide chemically synthesized
<220> FEATURE:
<221> NAME/KEY: REPEAT
<222> LOCATION: (1)..(1)
<223> OTHER INFORMATION: 0 to 10 repeats, wherein Xaa represents any
      amino acid
<220> FEATURE:
<221> NAME/KEY: REPEAT
<222> LOCATION: (9)..(9)
<223> OTHER INFORMATION: 0 to 10 repeats, wherein Xaa represents any
      amino acid

<400> SEQUENCE: 2

Xaa His Gly His Pro Phe Ala Pro Xaa
1               5

<210> SEQ ID NO 3
<211> LENGTH: 11
<212> TYPE: PRT
<213> ORGANISM: Artificial
<220> FEATURE:
<223> OTHER INFORMATION: Peptide chemically synthesized.
<220> FEATURE:
<221> NAME/KEY: REPEAT
<222> LOCATION: (1)..(1)
<223> OTHER INFORMATION: 0 to 10 repeats, wherein Xaa represents any
      amino acid
<220> FEATURE:
<221> NAME/KEY: DISULFID
<222> LOCATION: (2)..(10)
<220> FEATURE:
<221> NAME/KEY: REPEAT
<222> LOCATION: (11)..(11)
<223> OTHER INFORMATION: 0 to 10 repeats, wherein Xaa represents any
      amino acid

<400> SEQUENCE: 3

Xaa Cys Leu Ser Arg His Val Leu Gln Cys Xaa
1               5                   10

<210> SEQ ID NO 4
<211> LENGTH: 13
<212> TYPE: PRT
<213> ORGANISM: Artificial
<220> FEATURE:
<223> OTHER INFORMATION: Peptide chemically synthesized
<220> FEATURE:
<221> NAME/KEY: REPEAT
<222> LOCATION: (1)..(1)
<223> OTHER INFORMATION: 0 to 10 repeats, wherein Xaa represents any
      amino acid
<220> FEATURE:
<221> NAME/KEY: DISULFID
<222> LOCATION: (3)..(11)
<220> FEATURE:
<221> NAME/KEY: REPEAT
<222> LOCATION: (13)..(13)
<223> OTHER INFORMATION: 0 to 10 repeats, wherein Xaa represents any
      amino acid

<400> SEQUENCE: 4

Xaa Gly Cys Leu Ser Arg His Val Leu Gln Cys Ala Xaa
1               5                   10

<210> SEQ ID NO 5
<211> LENGTH: 11
<212> TYPE: PRT
<213> ORGANISM: Artificial
<220> FEATURE:
```

```
<223> OTHER INFORMATION: Peptide chemically synthesized
<220> FEATURE:
<221> NAME/KEY: REPEAT
<222> LOCATION: (1)..(1)
<223> OTHER INFORMATION: 0 to 10 repeats, wherein Xaa represents any
      amino acid
<220> FEATURE:
<221> NAME/KEY: DISULFID
<222> LOCATION: (2)..(10)
<220> FEATURE:
<221> NAME/KEY: REPEAT
<222> LOCATION: (11)..(11)
<223> OTHER INFORMATION: 0 to 10 repeats, wherein Xaa represents any
      amino acid

<400> SEQUENCE: 5

Xaa Cys His Gly His Pro Phe Ala Pro Cys Xaa
1               5                   10

<210> SEQ ID NO 6
<211> LENGTH: 13
<212> TYPE: PRT
<213> ORGANISM: Artificial
<220> FEATURE:
<223> OTHER INFORMATION: Peptide chemically synthesized
<220> FEATURE:
<221> NAME/KEY: REPEAT
<222> LOCATION: (1)..(1)
<223> OTHER INFORMATION: 0 to 10 repeats, wherein Xaa represents any
      amino acid
<220> FEATURE:
<221> NAME/KEY: DISULFID
<222> LOCATION: (3)..(11)
<220> FEATURE:
<221> NAME/KEY: REPEAT
<222> LOCATION: (13)..(13)
<223> OTHER INFORMATION: 0 to 10 repeats, wherein Xaa represents any
      amino acid

<400> SEQUENCE: 6

Xaa Gly Cys His Gly His Pro Phe Ala Pro Cys Ala Xaa
1               5                   10
```